(12) United States Patent
Dominick et al.

(10) Patent No.: US 9,251,312 B2
(45) Date of Patent: Feb. 2, 2016

(54) APPLICATION PLATFORM

(75) Inventors: Lutz Dominick, Eggolsheim (DE);
Karlheinz Dorn, Kalchreuth (DE);
Armin Michel, Erlangen (DE);
Vladyslav Ukis, Nürnberg (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 819 days.

(21) Appl. No.: 12/710,429

(22) Filed: Feb. 23, 2010

(65) Prior Publication Data

US 2011/0209139 A1    Aug. 25, 2011

(51) Int. Cl.
*G06F 19/00* (2011.01)
*G06F 11/07* (2006.01)
*G06F 9/445* (2006.01)

(52) U.S. Cl.
CPC .............. *G06F 19/3412* (2013.01); *G06F 8/65* (2013.01); *G06F 11/0796* (2013.01)

(58) Field of Classification Search
None
See application file for complete search history.

(56) References Cited

U.S. PATENT DOCUMENTS

| | | | |
|---|---|---|---|
| 6,618,735 B1 * | 9/2003 | Krishnaswami et al. | |
| 6,681,389 B1 * | 1/2004 | Engel et al. ................. | 717/173 |
| 6,859,923 B2 * | 2/2005 | Taylor ........................ | 717/172 |
| 8,074,213 B1 * | 12/2011 | Holtz ......................... | 717/172 |
| 2002/0174422 A1 * | 11/2002 | Kelley ................... | G06F 8/65 717/178 |
| 2004/0060044 A1 * | 3/2004 | Das ........................ | G06F 8/65 717/171 |
| 2004/0193917 A1 * | 9/2004 | Drews ........................ | 713/201 |
| 2005/0091535 A1 * | 4/2005 | Kavalam et al. ............ | 713/201 |
| 2006/0037012 A1 * | 2/2006 | Zomaya et al. ............. | 717/168 |
| 2006/0143606 A1 * | 6/2006 | Smith ................... | G06F 21/6218 717/175 |
| 2006/0174319 A1 * | 8/2006 | Kraemer et al. .................. | 726/1 |
| 2006/0191014 A1 * | 8/2006 | Zvi ........................ | G06F 8/67 726/26 |
| 2007/0143851 A1 * | 6/2007 | Nicodemus ............. | G06F 21/55 726/25 |
| 2007/0261047 A1 * | 11/2007 | Sah et al. ...................... | 717/168 |
| 2008/0143851 A1 * | 6/2008 | Shi ........................ | H04N 9/735 348/223.1 |
| 2008/0201701 A1 * | 8/2008 | Hofhansl et al. ............. | 717/168 |
| 2009/0144721 A1 * | 6/2009 | Wagner et al. ................ | 717/172 |

(Continued)

OTHER PUBLICATIONS

Abadi et al. Access Control in a World of Software Diversity. HotOS. 2005. Retrieved on [Sep. 14, 2015] Retrieved from the Internet: URL<http://static.usenix.org/legacy/events/hotos05/final_papers/full_papers/abadi/abadi_html/>.*

(Continued)

*Primary Examiner* — Thuy Dao
*Assistant Examiner* — Cheneca Smith
(74) *Attorney, Agent, or Firm* — Harness, Dickey & Pierce, P.L.C.

(57) ABSTRACT

An application platform is disclosed in a medical environment with a number of computer systems providing an information technology infrastructure and a plurality of basic information technology services to a number of users in the medical environment. At least one embodiment of the application platform provides a particularly simple and coordinated upgrade and update by independent software manufacturers and further provides a particularly high operational fail-safety during updates and upgrades by preventing damage to the systems caused by third party installer programs. To this end, at least one embodiment of the application platform includes a plurality of platform versioning building blocks and a number of platform data repositories, wherein the plurality of platform versioning building blocks are mutually independently updateable.

9 Claims, 2 Drawing Sheets

(56) References Cited

U.S. PATENT DOCUMENTS

2010/0153942 A1* 6/2010 Borissov ............... G06F 8/68
717/169
2010/0262958 A1* 10/2010 Clinton ............... H04W 8/245
717/171

OTHER PUBLICATIONS

Crameri et al. "Staged deployment in mirage, an integrated software upgrade testing and distribution system." ACM SIGOPS Operating Systems Review. vol. 41. No. 6. ACM, 2007, Retrieved on [Sep. 14, 2015] Retrieved from the Internet: URL<http://dl.acm.org/citation.cfm?id=1294283>.*

* cited by examiner

APPLICATION PLATFORM

FIELD

At least one embodiment of the present invention generally relates to an application platform in a medical environment with a number of computer systems providing an information technology infrastructure and a plurality of basic information technology services to a number of users in said medical environment.

BACKGROUND

The use of application platforms is generally well known in the prior art. Application platforms provide the necessary background for development, deployment, installation and execution of applications in environments with a number of computer systems. These systems are sometimes organized in a client-server structure and provide an information technology structure and a plurality of basic information technology services to the users of the environment. These services may include the management of identities and roles, libraries, security features, storage and persistence features, process identification and execution, deployment models etc.

Application platforms are used to benefit from the generic application infrastructure they provide. Applications may be selected and customized according to the needs of the users in the specific environment. The infrastructure of the platform allows developers to focus on the implementation of the features useful for the user within the applications without worrying about the general framework.

In order to be able to be customized according to the needs of the users of a specific environment, an application platform usually provides features and mechanisms for extensions and upgrades/updates. An update of the platform performed by a third party software manufacturer may extend the platform, extend the applications already installed on the platform or add new applications to the platform.

Operating systems usually provide generic installer programs such as e.g. the Windows installer that provide support and uniformity regarding software installations. Such installation programs are able to manage different versions of software products and their updates.

However, these installation programs do not provide functions to assure that an update or an extension of the platform does not destroy the already installed applications or the entire platform. This is especially important in the case of updates or extensions by third party installer programs and requires deeper insight into the structure of the application platform.

If damage is caused to the application platform by a third party installer program or other sources, this affects all applications installed on the platform that use the affected platform subsystems. These applications will no longer work normally. In the case of a client-server architecture where the platform is installed on a central server—which becomes more and more common especially in medical environments such as hospitals—all clients will stop operation.

SUMMARY

Due to the above shortcomings of the prior art, application platforms therefore lack operational security regarding the implementation of changes and updates to their installed applications and the fail-safety concerning the technical consequences of these changes to the application platform itself.

Accordingly, at least one embodiment of the present invention provides an application platform in a medical environment that provides system/method for a particularly simple and coordinated upgrade and update by independent software manufacturers.

At least one embodiment of the present invention assures a particularly high operational fail-safety of an application platform during updates and upgrades by preventing damage to the systems caused by third party installer programs.

At least one embodiment of the present invention ensures the integrity of an application platform while at the same time allow the installation of applications of arbitrary software manufacturers in a particularly efficient way.

To the accomplishment of the foregoing and related ends, the invention then comprises the features hereinafter fully described and particularly pointed out in the claims, the following description and drawings setting forth in detail certain illustrative embodiments of the invention, these being indicative, however, of but several of the various ways in which the principles of the invention may be employed.

BRIEF DESCRIPTION OF THE DRAWINGS

The present invention will become more fully understood from the detailed description of example embodiments given hereinbelow and the accompanying drawings, which are given by way of illustration only and are thus not limitive of the present invention, and wherein.

DETAILED DESCRIPTION OF THE EXAMPLE EMBODIMENTS OF THE PRESENT APPLICATION

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

Figure 1:
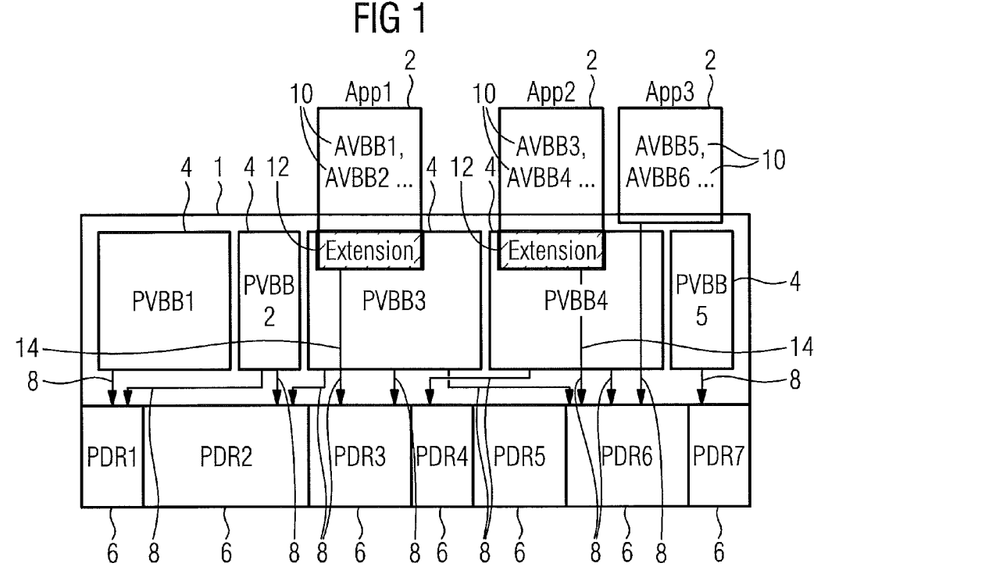
FIG. 1 illustrates a schematic diagram of an application platform according to an embodiment of the invention.

Referring to the drawing, FIG. 1 shows an application platform 1 for medical imaging, reporting, browsing, transfer and administration applications 2 in a medical environment. These applications 2 may be supplied by third party software manufacturers and therefore may not be developed by the same manufacturer as the application platform 1 itself. The application platform 1 provides an information technology infrastructure and a plurality of basic information technology services to the users in the medical environment such as the management of identities and roles, libraries, security features, storage and persistence features, process identification and execution, deployment models etc.

To ensure the integrity and operational safety of the already installed systems of the application platform 1 after and during and upgrade or update, the application platform is divided into a plurality of platform versioning building blocks (PVBBs) 4. The platform versioning building blocks 4 are mutually independent and may be separately versioned and updated. For reasons of better readability, FIG. 1 only shows five separate platform versioning building blocks 4, however the number of such platform versioning building blocks 4 may be considerably larger.

The platform versioning building blocks 4 defined in the medical application platform 1 according to a preferred embodiment are as follows:
i. Generic Reader Task
  1. Generic Viewing Master Page
  2. Basic Viewing Content Page
ii. Image Callup Task
  1. Image Callup Master Page
  2. External Callup Content Page
iii. Report Composer Task
  1. Report Composer Master Page
  2. Report Composer Content Page
  3. Basic Reporting Business Component
  4. Basic Results Business Component
  5. Report Template Data Service Component
  6. Evidence Documents Handling Service Component
  7. Common Reporting Data Remote Service Component
iv. Common Report Component
v. Taskflow Designer Task
vi. Task Pane Task
  1. Task Pane Master Page
  2. Task Pane Content Page
vii. Data Mapper Task
  1. Data Mapper Master Page
  2. Data Mapper Content Page
viii. Printing Task
  1. Basic Printing Business Component
  2. Print Service Component
  3. Windows Print Remote Service Component
ix. Preprocessing Task
  1. Preprocessing Job
x. Control Area Task
xi. Clinical Findings Navigator
xii. Data Publisher Task
  1. Data Publisher Job
xiii. Imaging Tools
xiv. Imaging Framework
  1. Basic Imaging Business Component
  2. Basic Layout Business Component
xv. Image Processing
  1. Scene Graph Service Component
  2. Imaging Data Service Component
  3. Display Service Component
  4. Processing Service Component
xvi. Pipeline
  1. Pipeline Service Component
xvii. Job Viewer
  1. Job Viewer Task
  2. Job Viewer Master Page
  3. Job Viewer Content Page
xviii. Patient Folder
  1. Patient Folder Task
  2. Patient Folder Master Page
  3. Order Content Page
xix. Browsing
  1. Generic Browser Task
  2. Generic Browser Master Page
  3. Worklist Data View Content Page
  4. Patient Tab Content Page
  5. Browsing Controls
  6. Browser Query Business Component
xx. Net Media
  1. Transfer Job Preparer Content Page
  2. DICOM Network Transfer Task
  3. DICOM Media Transfer Task
  4. DICOM Server Task
xxi. Service and Admin
  1. Service Portal Master Page
  2. Service Login Master Page
  3. DICOM Local Node Configuration Task
  4. DICOM Local Node Master Page
  5. DICOM Local Node General Content Page
  6. DICOM Local Node Worklist Content Page
  7. Edit Node Content Page 8. DICOM Remote Nodes Configuration Task
9. Remote Nodes Master Page
10. Remote Nodes List Content Page
11. Add Remote Node Content Page
12. Remote Node Storage Send Content Page
13. Remote Node Storage Receive Content Page
14. Site Info Master Page
15. Software Catalog Master Page
16. Software Catalog Form Content Page
17. Software Configuration Content Page
18. Message Viewer Task
19. Message Filter Master Page
20. Message Pattern Query Content Page
21. Pattern Admin Content Page
22. Related Messages Content Page
23. Siemens Remote Services Setup Master Page
24. Siemens Remote Services Connectivity Content Page
25. Remote Services Control Content Page
26. Remote Services Test Content Page
27. Mail Target Content Page
28. FTP Targets Content Page
29. System Message Bus Content Page
30. Auto Reporting Content Page
31. Utilization Management Content Page
32. File Transfer Master Page
33. Transfer Queue Form Content Page
34. Auto Report Form Master Page
35. Status Monitoring Master Page
36. User Profile Management Master Page
37. Service Level Mapper Master Page
38. License Admin Master Page
39. License Configuration Form Content Page
40. License Usage Content Page
41. License Reservation Content Page
42. License Details Content Page
43. Init Config Master Page
44. DICOM Media Compression Config Master Page
45. License Check Job Master Page
46. Log Statistics Job Master Page
47. Utilization Send Job Master Page
48. Silent Installation Job Master Page
49. HL7 Connection Config Task
50. HL7 Connection Config Master Page
51. Remote Desktop
52. Basic DICOM Device Nodes Business Component
53. Basic Silent Installation Business Component
54. License Configuration Remote Service Component
55. Site Info Remote Service Component
56. Siemens Remote Service Remote Service Component
57. DICOM Media Compression Configuration Remote Service Component
58. Autoreport Remote Service Component
59. File Transfer Remote Service Component
60. Software Catalog Remote Service Component
xxii. Web UI Framework
xxiii. Transfer Framework
1. Network Listener Task
2. Basic Transfer Business Component
3. Media Service Component
4. Network Service Component
5. Media Remote Service Component
xxiv. Data Management Framework
1. Data Management Job
2. Data Management Monitoring Task
3. Data Management Framework Configuration Service Component
4. Basic Data Business Component
5. XML Index Service Component
6. Data Access Service Component
7. Pixel Handling Service Component
8. File Storage Manger Service Component
9. File Access Service Component
xxv. Common Data Access Services
1. CDMA Service Component
2. File Access Remote Service Component
3. Information Model Manager
4. Memory Manager
5. Data Management Service Component
6. Data Management Remote Service Component
xxvi. Workflow Framework
1. Prefetch Task
2. Workflow Configuration
3. Basic Workflow Business Component
4. DICOM Worklist Access Service Component
5. Workflow Remote Service Component
6. Information Remote Service Component
xxvii. Protocol Management
1. Protocol Management Admin Task
2. Protocol Management Admin Master Page
3. Protocol Management Admin Content Page
4. Basic Protocol Business Component
5. Protocol Management Remote Service Component
6. Protocol Distribution Remote Service Component
xxviii. Operational Management
1. Asset Management
2. License Manager
3. Global Session Manager
4. Online Help Repository
5. System Status Monitoring Remote Service Component
6. Local Monitoring Service Remote Service Component
xxix. Enterprise Application Integration
1. Send Message Task Backend
2. Send Message Master Page
3. Basic Enterprise Application Integration Business Component
4. Information System Message Handling Service Component
xxx. Technical Architecture
1. Central Strategy Manager
2. Load Balancer
3. System Service Bus
4. Bootstrapper
5. Vortal
6. Starter
7. Libraries
xxxi. Application Infrastructure
1. System Diagnostics Task
2. System Diagnostics Master Page
3. Security Provider
4. Configuration Infrastructure Service
5. Logging Infrastructure Service
6. Licensing Infrastructure Service
7. Auditing Infrastructure Service
8. Tracking Infrastructure Service
9. Session Management Infrastructure Service
10. Context Management Infrastructure Service
11. Security Infrastructure Service
12. Utilization Infrastructure Service
13. Installation Infrastructure Service
14. System Diagnostics Infrastructure Service
15. Online Help Infrastructure Service
16. Lifecycle Management Infrastructure Service
17. Online Help Viewer
18. Platform Installer The application platform 1 further comprises a number of platform data repositories (PDRs) 6 that provide data to the platform versioning building blocks 4. Again, for reasons of better readability, FIG. 1 only shows seven separate platform data repositories 6, however the number of such platform data repositories 6 may be considerably larger. In the preferred embodiment, the following platform data repositories 6 are defined:

i. Acquisition Protocols Templates Repository
ii. Acquisition Protocols Repository
iii. Central Log Repository
iv. Central Audit Repository
v. Central Utilization Repository
vi. RIS Workflow Data Repository
vii. PACS Study Repository
viii. Authorization Repository
ix. Configuration Repository
x, Application Context Folder
xi. Deployment Server
xii. Global Binary Cache
xiii. Memory Manager
xiv. Lifecycle Manager Repository
xv. License Repository
xvi. Software Depot
xvii. Report Templates Repository
xviii. Short Term Storage (for medical images)
xix. Application Templates Repository
xx. Task Templates Repository
xxi. System Service Bus Configuration Repository
xxii. User Repository
xxiii. DICOM Configuration Repository
xxiv. Online Help Repository
xxv. Display and Data Protocols Repository The platform versioning building blocks 4 have a cycle-free and clear hierarchy, i.e. there are no mutual dependencies. This allows a separate update of each platform versioning building block 4 and the extension of the application platform 1 through adding of further platform versioning building blocks 4. Also, each platform versioning building block 4 can be extended separately.

Most, but not necessarily all platform versioning building blocks 4 have a number of assignments 8 to the platform data repositories 6. These assignments 8 may either constitute a hierarchical ownership of the respective platform versioning building block 4 or they may simply show the fact that a respective platform versioning building block 4 uses the data in a specific platform data repository 6.

For each assignment 8 of a platform versioning building block 4 to a platform data repository 6, a number of allowed actions is predefined. These actions are chosen from the group of creating, reading, updating, deleting or executing. In the preferred embodiment a platform versioning building block 4 hierarchically owning a platform data repository 6 is allowed writing accesses such as updating or deleting, whereas a platform versioning building block 4 simply using a platform data repository 6 is only allowed to read data from that platform data repository 6.

When an application 2 is installed on the application platform 1 to provide additional information technology services to the users of the application platform 1, a number of application versioning building blocks (AVBBs) 10 associated with the application 2 are deployed on the application platform 1. As shown in FIG. 1, an application versioning building block 10 may, but need not extend a platform versioning building block 4, thus forming an extension of said platform versioning building block 4. The extension is performed with the means provided and defined by the platform versioning building blocks 4 such as plug-ins. The application versioning building blocks 10 may also use platform data repositories 6, indicated by assignments 14. The platform versioning building block 4 owning the respective platform data repository then defines the actions (creating, reading, updating, deleting or executing) allowed to the application versioning building block 10. Because of the mutually independent structure of the application platform 1 according to embodiments of the present invention, multiple versions of an application versioning building block 10 may be deployed side-by-side. Furthermore, the applications may be delivered by different software manufacturers.

Figure 2:
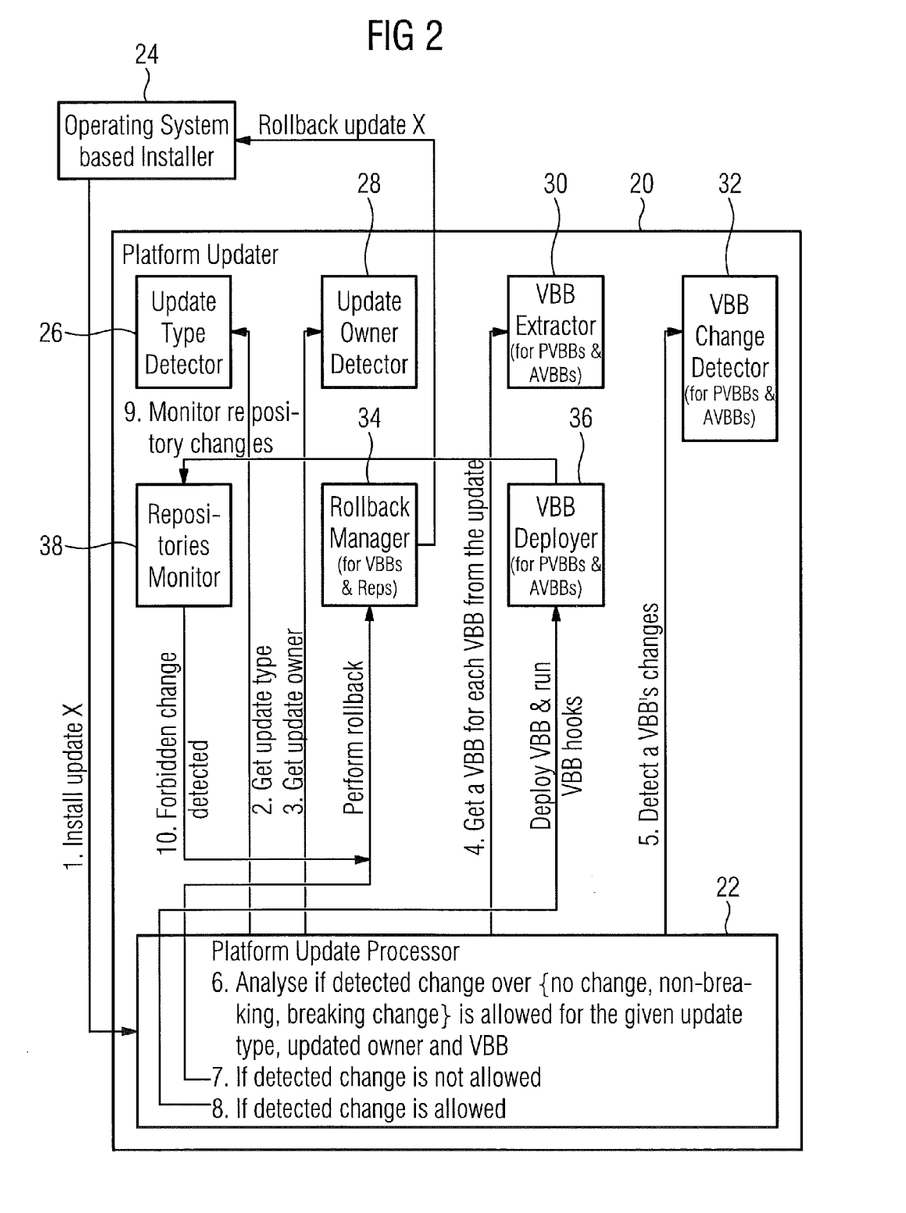
FIG. 2 shows an example embodiment of a platform updater module according to the invention.

The application platform further comprises a platform updater module 20, shown in FIG. 2. The platform updater module provides a limited number of predefined update types: HotFix, Application Update, and Platform Update. For each update type, a specific set of actions chosen from the group of creating an application versioning building block, extending an application versioning building block, creating a platform versioning building block, extending a platform versioning building block and changing data in a platform data repository is allowed. The allowed actions vary depending on whether the update is effected by the application platform manufacturer or a third party software company.

Preferably, the allowed actions are further restricted if the update is effected by independent third party software. In the preferred embodiment, the allowed actions for each update type are shown in the following tables:

i. HotFix

|  |  | Platform in vendor installs Hotfix | Independent software vendor installs Hotfix |
|---|---|---|---|
| Change of installed platform | Creating a PDR | Allowed according to the enabled actions for each PDR |  |
|  | Extending a PDR |  |  |
|  | Creating an AVBB | Forbidden | Forbidden |
|  | Extending an AVBB | Forbidden | Allowed |
|  | Creating a PVBB | Forbidden | Forbidden |
|  | Extending a PVBB | Allowed non-breaking | Forbidden | ii. Application Update

|  |  | Platform vendor installs (as part of) Application Update | Independent software vendor installs Application Update |
|---|---|---|---|
| Change of installed platform | Creating a PDR | Allowed according to the enabled actions for each PDR |  |
|  | Extending a PDR |  |  |
|  | Creating an AVBB | Forbidden | Allowed |
|  | Extending an AVBB | Forbidden | Allowed |
|  | Creating a PVBB | Allowed | Forbidden |
|  | Extending a PVBB | Allowed non-breaking | Allowed | iii. Platform Update

|  |  | Platform vendor installs Platform Update | Independent software vendor installs (as part of) Platform Update |
|---|---|---|---|
| Change of installed platform | Creating a PDR | Allowed according to the enabled actions for each PDR |  |
|  | Extending a PDR |  |  |
|  | Creating an AVBB | Forbidden | Allowed |
|  | Extending an AVBB | Forbidden | Allowed |
|  | Creating a PVBB | Allowed | Forbidden |
|  | Extending a PVBB | Allowed | Allowed |

As a component of the platform updater module 20 according to an embodiment of the invention, the platform update processor 22 coordinates the update and ensures that only the actions allowed to the specific update type are performed. To this end, the platform updater module 20 further comprises the components shown in FIG. 2.

An operating system based installer 24 such as a Windows installer tries to apply an update or an extension of the application platform 1 and thus invokes the platform updater module 20 and the platform updater processor 22. The platform updater module 20 comprises an update type detector 26 to choose and assign a predefined update type (Hot-Fix, Application Update, Platform Update) to the installer 24. Furthermore, the platform updater module 20 comprises an update owner detector 28 to determine whether the installer 24 is manufactured by the platform vendor or an independent third party company. According to the assigned update type and the detected update owner, the set of allowed actions is assigned to the installer 24.

The platform updater module 20 comprises a versioning building block extractor 30 to extract the independent platform versioning building blocks 4 and application versioning building blocks 10 to be updated. The installer 24 then applies the intended changes. The platform updater module 20 further comprises and a versioning building block change detector 32 to detect the changes to the versioning building blocks 4, 10 caused by the installer 24.

The platform update processor 22 then analyses if the detected change is allowed for the given update type, update owner, and versioning building blocks 4, 10. If the detected change is not allowed, the platform update processor invokes a rollback manager 34 which undoes the specific action or change and sets the system back into its prior state. The rollback manager 34 may even cancel execution of the installer 24. If the detected change is allowed, the platform update processor 22 invokes the versioning building block deployer 36 which deploys the changed or added versioning building blocks 4, 10 and platform data repositories 6 to the application platform 1.

Changes to the platform data repositories 6 are detected by the repositories monitor 38. If a forbidden change is detected, the rollback manager 34 is again invoked to undo the performed changes.

The solution according to the invention makes it possible to perform platform updates by independent software manufacturers such that changes to the platform are permanently controlled. This ensures that the already installed platform is not destroyed by the update.

An embodiment of the invention suggests to create a strict, non-cyclic hierarchy of versioning building blocks which provide the platform functionality. The hierarchy allows a separate update of single platform versioning building blocks, contrary to the methods of the prior art, which only allows the update of an entire platform.

Furthermore, the invention defines update types being assigned allowed changes to the platform (PVBBs and PDRs). The changes invoked by an installer are permanently controlled by a platform updater module. Changes to the platform (changes to the code of PVBBs, AVBBs and PDRs) are explicit, vary by update type and are consequently constrained. The invention may be used in connection with a standard Windows installer and may be generalized to software platforms of arbitrary domains.

A latitude of modification, change and substitution is intended in the foregoing disclosure and in some instances some features of the invention will be employed without a corresponding use of other features. Accordingly, it is appropriate that the appended claims be construed broadly and in a manner consistent with the spirit and scope of the invention herein.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combineable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A non-transitory computer-readable medium on which an application platform for use in a medical environment with a number of computer systems is stored, the application platform providing an information technology infrastructure and a plurality of basic information technology services to a number of users in said medical environment, at least one application being installable on the application platform to provide additional information technology services to the users of the application platform, the application platform comprising:
   a plurality of platform versioning building blocks;
   a number of platform data repositories, said plurality of platform versioning building blocks being mutually independently updateable; and
   a platform updater module configured to,
      provide a limited number of predefined update types selected from a group of a Hotfix, a Platform Update and an Application Update, each of said predefined update types being configured to allow a specific set of allowed actions,
      choose and assign one of said predefined update types to an update program applied to the application platform,
      determine access of said update program on the application platform to the set of allowed actions of the chosen and assigned update type based on a manufacturer of the update program,
      extract the platform versioning building blocks and application versioning building blocks to be updated by the update program,
      apply the update program to the extracted platform versioning building blocks and the application versioning building blocks and detect changes to the platform versioning building blocks and the application versioning building blocks caused by the update program,
      analyze if the detected changes are allowed for the given update type assigned to the update program, and
      undo the changes if the changes are not allowed; and
   a number of application versioning building blocks associated with an application providing a number of information technology services,
      wherein a number of said platform versioning building blocks are respectively assigned to a number of said platform data repositories,
      wherein said platform data repositories are at least one of hierarchically owned and used by said respective platform versioning building block,
      wherein for each of said assignments of the number of platform versioning building blocks to the number of platform data repositories, a number of allowed actions is predefined,
      wherein said number of allowed actions is chosen from a group of creating, reading, updating, deleting and executing,
      wherein the number of said application versioning building blocks extends the number of said platform versioning building blocks, and
      wherein the number of said application versioning building blocks is respectively assigned to the number of said platform data repositories.

2. The non-transitory computer-readable medium of claim 1, wherein said platform versioning building blocks form a cycle-free hierarchy.

3. The non-transitory computer-readable medium of claim 2, wherein the set of allowed actions is chosen from a group including creating an application versioning building block, extending an application versioning building block, creating a platform versioning building block, extending a platform versioning building block, and changing data in one of the number of platform data repositories.

4. The non-transitory computer-readable medium of claim 1, wherein the set of allowed actions in a predefined update type is chosen from a group of creating an application versioning building block, extending an application versioning building block, creating a platform versioning building block, extending a platform versioning building block and changing data in a platform data repository.

5. The non-transitory computer-readable medium of claim 4, wherein the set of allowed actions in a predefined update type is further restricted upon said update program being a third party program.

6. The non-transitory computer-readable medium of claim 1, wherein the platform updater module is configured to determine the access such that the set of allowed actions includes fewer allowed actions if the manufacturer is a third party company than if the manufacturer is a vendor of the application platform.

7. A non-transitory computer-readable medium on which an application platform for use in a medical environment with a number of computer systems is stored, the application platform providing an information technology infrastructure and a plurality of basic information technology services to a number of users in said medical environment, at least one application being installable on the application platform to provide additional information technology services to the users of the application platform, the application platform comprising:
   a plurality of platform versioning building blocks, said platform versioning building blocks forming a cycle-free hierarchy;
   a number of platform data repositories, said plurality of platform versioning building blocks being mutually independently updateable; and
   a platform updater module configured to,
      provide a limited number of predefined update types selected from a group of a Hotfix, a Platform Update and an Application Update, each of said predefined update types being configured to allow a specific set of allowed actions,
      choose and assign one of said predefined update types to an update program applied to the application platform,
      determine access of said update program on the application platform to the set of allowed actions of the chosen and assigned update type based on a manufacturer of the update program, extract the platform versioning building blocks and application versioning building blocks to be updated by the update program, apply the update program to the extracted platform versioning building blocks and the application versioning building blocks and detect changes to the platform versioning building blocks and the application versioning building blocks caused by the update program, analyze if the detected changes are allowed for the given update type assigned to the update program, and undo the changes if the changes are not allowed.

8. The non-transitory computer-readable medium of claim 7, wherein the platform updater module is configured to determine the access such that the set of allowed actions includes fewer allowed actions if the manufacturer is a third party company than if the manufacturer is a vendor the application platform.

9. The non-transitory computer-readable medium of claim 7, wherein the set of allowed actions is chosen from a group including creating an application versioning building block, extending an application versioning building block, creating a platform versioning building block, extending a platform versioning building block, and changing data in one of the number of platform data repositories.

* * * * *